(12) United States Patent
Hirose et al.

(10) Patent No.: US 8,797,544 B2
(45) Date of Patent: Aug. 5, 2014

(54) OPTICAL COHERENCE TOMOGRAPHIC IMAGING DEVICE AND IMAGING METHOD OF OPTICAL COHERENCE TOMOGRAPHIC IMAGE

(75) Inventors: Futoshi Hirose, Yokohama (JP); Kazuhide Miyata, Yokohama (JP); Kazuro Yamada, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 312 days.

(21) Appl. No.: 12/464,422

(22) Filed: May 12, 2009

(65) Prior Publication Data

US 2009/0285354 A1 Nov. 19, 2009

(30) Foreign Application Priority Data

May 19, 2008 (JP) ................................ 2008-130392

(51) Int. Cl.
*G01B 11/02* (2006.01)

(52) U.S. Cl.
USPC .......................................... 356/497; 356/479

(58) Field of Classification Search
USPC ................................................. 356/479, 497
See application file for complete search history.

(56) References Cited

U.S. PATENT DOCUMENTS

| | | | |
|---|---|---|---|
| 5,644,642 A * | 7/1997 | Kirschbaum | ................. 382/103 |
| 6,155,683 A | 12/2000 | Hanaki et al. | |
| 7,236,251 B2 | 6/2007 | Takaoka | ........................ 356/497 |
| 7,510,282 B2 | 3/2009 | Ueno et al. | |
| 7,749,216 B2 | 7/2010 | Sumiya | |
| 2006/0084956 A1 | 4/2006 | Sumiya | |
| 2008/0024721 A1 | 1/2008 | Ueno et al. | |
| 2009/0091766 A1 | 4/2009 | Hirose | |

FOREIGN PATENT DOCUMENTS

| | | |
|---|---|---|
| JP | 11-276439 A | 10/1999 |
| JP | 2001-275976 A | 10/2001 |
| JP | 2002-174769 | 6/2002 |
| JP | 2006-051101 A | 2/2006 |
| JP | 2006-212153 A | 8/2006 |
| JP | 2008-006104 A | 1/2008 |
| JP | 2008-029467 A | 2/2008 |

* cited by examiner

*Primary Examiner* — Tarifur Chowdhury
*Assistant Examiner* — Jonathon Cook
(74) *Attorney, Agent, or Firm* — Fitzpatrick, Cella, Harper & Scinto

(57) ABSTRACT

An optical tomographic imaging device and the like which suppress influence in the case of a measuring beam being truncated by an iris, and can ensure reliability of a tomographic image which is acquired, when imaging the tomographic image of a retina in an eyeground of an examined eye. An optical tomographic imaging device is configured to have an observation unit observing a state of irradiating an examined object with the measuring beam, and imaging a state of the measuring beam being incident on the examined object as an observation image, a recording unit recording the observation image by linking the observation image with a tomographic image by the optical tomographic imaging device, and an evaluating unit evaluating reliability of the tomographic image which is linked with the observation image based on the observation image imaged in the observation unit.

17 Claims, 5 Drawing Sheets

OPTICAL COHERENCE TOMOGRAPHIC IMAGING DEVICE AND IMAGING METHOD OF OPTICAL COHERENCE TOMOGRAPHIC IMAGE

BACKGROUND OF THE INVENTION

1. Field of the Invention

The present invention relates to an optical coherence tomographic imaging device and an imaging method of an optical coherence tomographic image, and particularly relates to an optical coherence tomographic imaging device and an imaging method of an optical coherence tomographic image used in ophthalmic diagnosis, treatment, and the like.

2. Description of the Related Art

Various ophthalmologic apparatuses using optical devices are used at present.

For example, as for optical devices for observing eyes, various kinds of devices such as an anterior ocular segment photographing device, a fundus camera, and a confocal scanning laser ophthalmoscope (Scanning Laser Ophthalmoscope: SLO) are used.

Among them, an optical coherence tomographic imaging device by optical coherence tomography (OCT) using multi-wavelength light wave coherence can obtain a tomographic image of a specimen at high resolution. The device is on the way to becoming indispensable in outpatient clinics specialized in retinas as an ophthalmologic device.

Hereinafter, the device will be described as an OCT device.

According to the above described OCT device, a sample is irradiated with a low coherent light, and the reflected light from the sample can be measured at high sensitivity by using a coherent system.

Further, the OCT device can obtain a tomographic image at high resolution by scanning the low coherent light over the sample.

Therefore, the OCT device can image the tomographic image of the retina in the eyeground of an examined eye. Thus, the OCT devices are widely used in the ophthalmologic diagnosis of retinas.

Meanwhile, in recent years, there has been a growing demand for obtaining tomographic images at high resolution in such optical coherence tomographic imaging devices.

Therefore, various devices have been conventionally developed. Japanese Patent Application Laid-Open No. 2002-174769 discusses an optical device for observing the inside of a biological specimen by properly using an OCT and OCM (Optical Coherence Microscopy).

In this device, the OCT is used for checking a large structure in a biological specimen, and the OCT can be switched to the OCM when observing a notable region in the structure with higher resolution.

At this time, since the OCT and OCM differ greatly in depth of focus (DOF), a beam diameter converting optical system is used so that the beam diameters corresponding to the OCT having a small numerical aperture and the OCM having a large numerical aperture can be set, and observation at a high Signal-to-Noise (S/N) ratio can be made.

SUMMARY OF THE INVENTION

When ophthalmologic diagnosis of a retina is performed by the OCT device, it is sometimes difficult for the measuring beam to pass through a pupil without being truncated by an iris and form an image at a desired position of the retina for the reason that it is difficult to keep the examined eye at a standstill.

When the measuring beam is truncated by the iris, the ratio of the measuring light reaching the desired position of the retina in the OCT device decreases, and the reflected beam from the retina decreases correspondingly. Thus, reliability of the tomographic image becomes relatively low. Therefore, it is necessary to consider how to handle these problems.

However, in the device in Japanese Patent Application Laid-Open No. 2002-174769 of the prior art described above, the problem as described above which occurs when the measuring beam is truncated by the iris in the OCT device is not taken into consideration.

Specifically, in Japanese Patent Application Laid-Open No. 2002-174769, the OCT and OCM, differing significantly in depth of focus (DOF), are configured to be switchable by using the beam diameter converting optical system, so that the mode by the OCT capable of wide-range observation and the mode by the OCM capable of high-resolution observation can be properly used. However, the above described problem is not considered at all.

Describing the above in more detail, when ophthalmologic diagnosis of a retina is performed by the OCT device, the measuring beam that is a low coherent beam is caused to form an image at a desired position of the retina, and a tomographic image is acquired.

However, due to the factor of the examined eye such as weakening of eyesight, it is sometimes difficult to cause the measuring beam to form an image at a desired position of the retina.

That is to say, in the OCT device, each of the measuring beams is truncated by the iris. Thereby, the ratio of the measuring beam reaching the desired position of the retina decreases, and the reflected beam from the retina sometimes decreases correspondingly.

In such a case, the resultant tomographic image may have low contrast since there is an upper limit to the power of the measuring beam for ensuring safety.

Further, in such a case, reliability of the tomographic image becomes relatively low, and therefore, in the diagnosis using the tomographic image, these problems need to be considered.

Especially when the beam diameter of the measuring beam is configured to be large for the purpose of obtaining the OCT device with high resolution in the direction perpendicular to the optical axis, the tendency is more remarkable.

When Rayleigh's theory is used here, the resolution $\delta$ in the direction perpendicular to the optical axis of the OCT device is expressed by $\delta = (0.61 \times \lambda)/NA$.

Here, NA represents the numerical aperture of the objective lens, and $\lambda$ represents the wavelength of the measuring beam. For example, when the beam diameter of the measuring beam is set as 4 mm, the diameter of the eyeball is set as 23 mm, the refractive index of the eyeball is set as 1.33, and the wavelength of the measuring light is set as 830 nm, the resolution $\delta$ is 4.4 μm.

As is obvious from the above description, when opthalmologic diagnosis of an retina is performed by the OCT device, it becomes a problem as to how to handle the case where the measuring beam is truncated by the iris, but in the above described prior art and the like, consideration is not given to such a problem.

In view of the above described problem, the present invention has an object to provide an optical tomographic imaging device and an imaging method of an optical tomographic image which suppress influence when a measuring beam is truncated by an iris and can ensure reliability of an tomographic image to be acquired, especially when imaging the tomographic image of the retina in the eyeground of an examined eye.

The present invention provides an optical tomographic imaging device and an imaging method of an optical tomographic image which are configured as follows.

An optical tomographic imaging device of the present invention is an optical tomographic imaging device dividing a light from a light source into a measuring beam and a reference beam, guiding the measuring beam to an examined object and guiding the reference beam to a reference mirror, and imaging a tomographic image of the examined object by using a return beam by the measuring beam which is reflected or scattered by the examined object, and the reference beam reflected by the reference mirror, and is characterized by including an observation unit observing a state of irradiating the examined object with the measuring beam, and imaging a state of the measuring beam being incident on the examined object as an observation image, a recording unit recording the observation image by linking the observation image with the tomographic image by the optical tomographic imaging device, and an evaluating unit evaluating reliability of the tomographic image which is linked with the observation image based on the observation image imaged in the observation unit.

Further, an imaging method of an optical tomographic image of the present invention is an imaging method of an optical tomographic image dividing a light from a light source into a measuring beam and a reference beam, guiding the measuring beam to an examined object and guiding the reference beam to a reference mirror, and imaging a tomographic image of the examined object by using a return beam by the measuring beam reflected or scattered by the examined object and the reference beam reflected by the reference mirror, and is characterized by including recording the observation image by linking the observation image with the tomographic image by the optical tomographic imaging device, evaluating reliability of the tomographic image linked with the observation image based on the observation image imaged in the observation unit, and stopping imaging of the tomographic image or re-imaging the tomographic image based on the evaluation of the evaluating unit.

Further, a computer-readable storage medium according to another aspect of the present invention is characterized by storing a program for causing a computer to execute an imaging method of an optical coherence tomographic image.

Further, a program according to another aspect of the present invention is characterized by causing a computer to execute the imaging method of an optical coherence tomographic image.

Further, an optical coherence tomographic imaging device of another aspect of the present invention is an optical coherence tomographic imaging device dividing a light from a light source into a measuring beam and a reference beam, guiding the measuring beam to an examined object and guiding the reference beam to a reference mirror, and imaging a tomographic image of the examined object by using a return beam by the measuring beam which is reflected or scattered by the examined object, and the reference beam reflected by the reference mirror, and is characterized by including an observation unit observing a state of irradiating the examined object with the measuring beam, and imaging a state of the measuring beam being incident on the examined object as an observation image, a recording unit recording the observation image and the tomographic image by linking the observation image and the tomographic image with each other, and an evaluating unit evaluating the tomographic image which is linked with the observation image based on the observation image imaged in the observation unit.

Further, an optical coherence tomographic imaging device according to another aspect of the present invention is characterized by including an observation image information acquiring unit for acquiring a state of irradiating an examined object with a measuring beam as observation image information, a detection unit for detecting a combined beam of a return beam which is the measuring beam reflected or scattered by the examined object and a reference beam, and a tomographic image information acquiring unit for acquiring tomographic image information of the examined object from the combined beam detected by the detection unit, and is characterized in that the observation image information acquired by the observation image information acquiring unit is configured to be linked with each of the tomographic image information obtained by irradiating the examined object with the measuring beam.

According to the present invention, an optical tomographic imaging device, which suppresses influence in the case where a measuring beam is truncated by an iris and can ensure reliability of the tomographic image which is acquired, when imaging a tomographic image which is acquired, when imaging a tomographic image of a retina in an eyeground of an examined eye by an O T device, and an optical tomographic image, can be realized.

Further features of the present invention will become apparent from the following description of exemplary embodiments with reference to the attached drawings.

DESCRIPTION OF THE EMBODIMENTS

Figure 1:
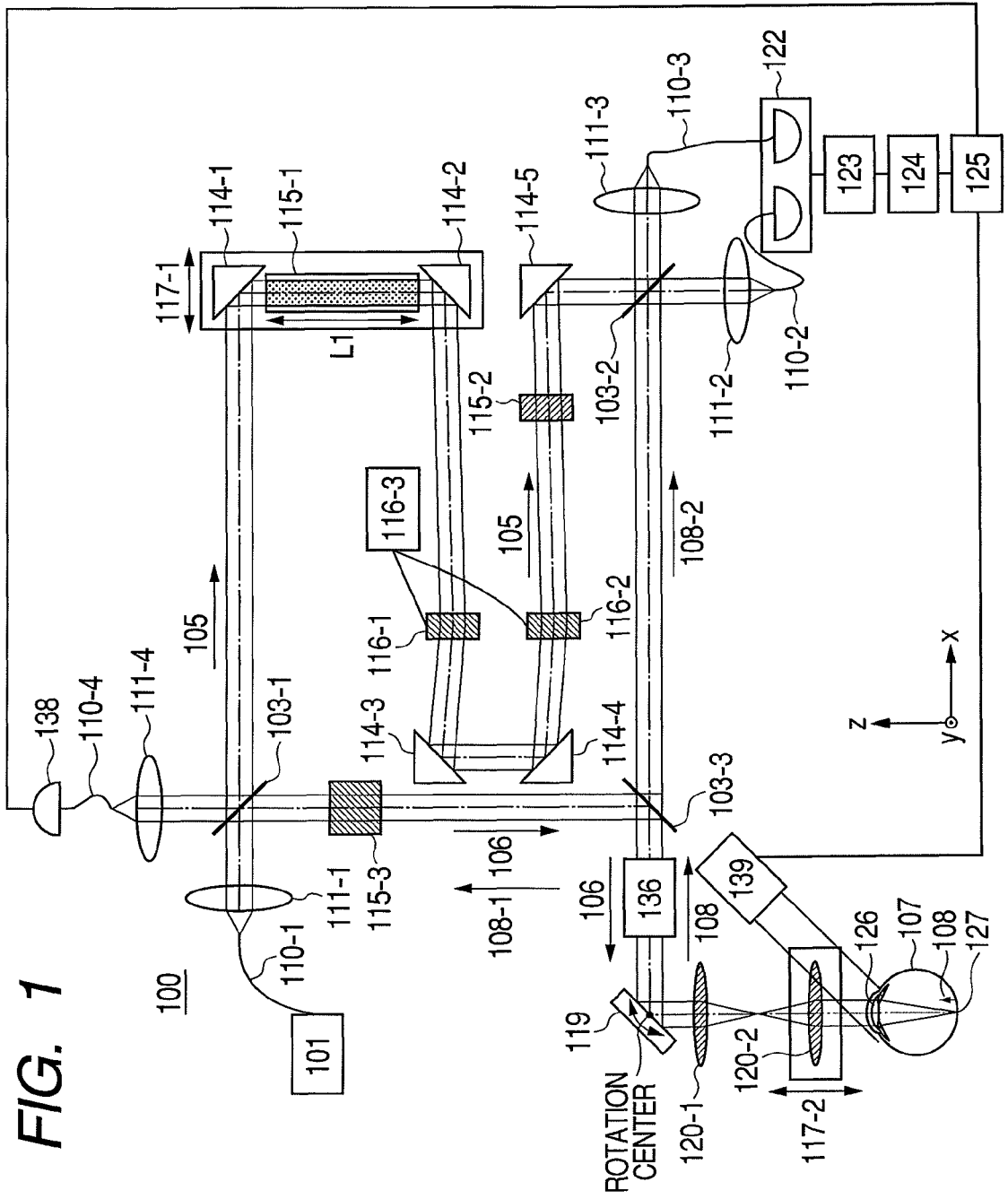
FIG. 1 is a view illustrating a schematic configuration of an entire optical system of an OCT device in embodiment 1 of the present invention.

Next, an OCT device in an embodiment of the present invention will be described.

In an OCT device of the present embodiment, an optical tomographic imaging device dividing a light from a light source into a measuring beam and a reference beam, guiding the measuring beam to an examined object and guiding the reference beam to a reference minor, and imaging a tomographic image of the examined object by using a return beam by the measuring beam which is reflected or scattered by the examined object, and the reference beam reflected by the reference mirror, includes an observation unit.

The observation unit is configured to observe a state of irradiating the examined object with the measuring beam, and image a state of the measuring beam being incident on the examined object as an observation image.

Further, the OCT device includes a recording unit recording the observation image by linking the observation image with the tomographic image by the optical tomographic imaging device, and an evaluating unit evaluating the reliability of the tomographic image which is linked with the observation image based on the observation image imaged in the observation unit.

Thereby, the incident state of the measuring beam on the examined object is grasped by the observation unit, and reliability of the tomographic image linked with the observation image can be examined.

At this time, imaging of the tomographic image is configured to be stopped, or to be capable of being performed again based on the evaluation of the evaluating unit, whereby reliability of the tomographic image can be ensured.

Further, in the OCT device, the evaluating unit can be configured to include a unit evaluating the reliability by a value of an area of the measuring beam with which a portion except for a pupil of the eye is irradiated when an eye is examined as the examined object.

Alternatively, the evaluating unit can be configured to include a unit evaluating the reliability by a value of a distance between relative positions of the pupil of the eye and the measuring beam when an eye is examined as the examined object.

Alternatively, the evaluating means can be configured to include a unit evaluating the reliability by a shape of the measuring beam in a portion irradiated with the measuring beam except for the pupil of the eye when an eye is examined as the examined object.

By them, the degree of irradiation of the measuring beam with which the portion except for the pupil is irradiated can be quantitatively grasped.

Further, the OCT device can be configured to have a reporting unit reporting an evaluation result acquired by the evaluating unit.

When a rank acquired by using the unit which performs evaluation is a desired rank, the device can shift to the next operation of stopping imaging or re-imaging quickly as a result of having such a reporting unit.

Further, in the OCT device, the observation unit can be configured by a camera.

Alternatively, the observation unit can be configured by an area sensor.

Alternatively, the observation unit can be configured by a confocal microscope.

By them, the state of the measuring beam being incident on the pupil can be easily observed.

Further, in the OCT device, at least any one of an optical path guiding the light from the light source to a position where the light is divided into a measuring beam and a reference beam, an optical path guiding the measuring beam to an examined object, an optical path guiding the return beam to a photoelectric conversion circuit, and an optical path guiding the reference beam to the photoelectric conversion circuit, can be configured by an optical fiber.

Thereby, a compact optical coherence tomographic imaging device excellent in stability can be realized.

Further, in the present embodiment, an optical tomographic image can be imaged by the following steps when the imaging method of an optical tomographic image is carried out by using the OCT device.

In a first step, the observation image is recorded by being linked with the tomographic image by the optical tomographic imaging device.

Next, in a second step, reliability of the tomographic image linked with the observation image is evaluated based on the observation image imaged in the observation unit.

Next, in a third step, imaging of the tomographic image is stopped, or the tomographic image is re-imaged based on evaluation of the evaluating unit.

Thereby, reliability of the tomographic image can be ensured.

At this time, at least one of the first step to the third step is configured to be automatically performed, and thereby, an efficient imaging system of a tomographic image which can ensure reliability of the tomographic image can be realized.

EMBODIMENTS

Next, embodiments of the present invention will be described.

Embodiment 1

In embodiment 1, an OCT device to which the present invention is applied will be described.

In the present embodiment, TD-OCT (Time Domain OCT) which specially acquires a tomographic image of a retina of an eye will be described.

However, the present invention can be applied to not only such TD-OCT but also to FD-OCT (Fourier Domain OCT).

First, a schematic configuration of an entire optical system of the OCT device in the present embodiment will be described.

FIG. 1 illustrates a view about the schematic configuration of the entire optical system of the OCT device in the present embodiment.

In FIG. 1, in an OCT device 100, a light source 101, beam splitters 103, a reference beam 105, a measuring beam 106, an eye 107, a return beam 108, single mode fibers 110, lenses 111 and 120, and mirrors 114 are set.

In the OCT device 100, dispersion compensating glasses 115, acousto-optic modulating devices 116-1 and 116-2, a controller 116-3, electric stages 117, an XY scanner 119, a balanced detector 122, an amplifier 123, a filter 124, and a personal computer 125 are also installed.

In the OCT device, a cornea 126, a retina 127, a variable beam expander 136, a detector 138, and an observation camera 139 are also set.

The OCT device 100 of the present embodiment configures a Mach-Zehnder interferometer as a whole as shown in FIG. 1.

In FIG. 1, light emitted from the light source 101 is divided into the reference beam 105 and the measuring beam 106 by a beam splitter 103-1.

The measuring beam 106 becomes the return beam 108 which is reflected or scattered by the eye 107 that is an observation target and is returned, and is divided into a return beam (first return beam) 108-1 and a return beam (second return beam) by a beam splitter 103-3. Of these return beams, the return beam 108-2 is combined with the reference beam 105 by a beam splitter 103-2.

After the reference beam 105 and the return beam 108-2 are combined, they are divided by the beam splitter 103-2, and are incident on the balanced detector 122.

The balanced detector 122 converts light intensity into a voltage, and with use of the signal of the voltage, the tomographic image of the eye 107 is configured.

Next, the light source 101 and its periphery will be described.

The light source 101 is a SLD (Super Luminescent Diode) which is a typical low-coherent light source.

Its wavelength is 830 nm, and the bandwidth is 50 nm. Here, the bandwidth is an important parameter, because the bandwidth influences the resolution in the optical axis direction of the tomographic image to be acquired.

Further, any kind of light source may be used as long as it can emit a low-coherent light, though the SLD is selected here, and an ASE (Amplified Spontaneous Emission) and the like can be used.

Further, considering measurement of an eye, near-infrared light is suitable as the wavelength. Since the wavelength influences the resolution in the lateral direction of the tomographic image to be acquired, the wavelength is desirably as short as possible, and therefore, 830 nm is selected here.

Depending on the measured site of the observation target, other wavelengths may be selected.

The light which is emitted from the light source 101 is guided to a lens 111-1 through a single-mode fiber 110-1, and is regulated to be parallel beams with a beam diameter of 4 mm.

Next, an optical path of the reference beam 105 will be described.

The reference beam 105 which is divided by the beam splitter 103-1 is successively incident on reference mirrors 114-1 to 114-5 to change direction, and thereby, is incident on the balanced detector 122 by the beam splitter 103-2.

Here, dispersion compensating glasses 115-1 to 115-2 are used. The length of the dispersion compensating glass 115-1 is L1, which is desirably equal to twice as long as the depth of an ordinary eye.

The dispersion compensating glass 115-1 compensates dispersion when the measuring beam 106 goes to and returns from the eye 107 with respect to the reference beams 105.

Here, L1 is set so that L1=46 mm that is twice as long as 23 mm, which is the diameter of the average eyeball of a person from Japan. Further, an electric stage 117-1 can move in the direction illustrated by the arrow, and can regulate and control the optical path length of the reference beam 105.

Next, a modulation method of the reference beam 105 will be described.

Here, a controller 116-3 is a controller for acousto-optic modulating devices 116-1 and 116-2.

Further, the two acousto-optic modulating devices 116-1 and 116-2 are used as shifters of an optical frequency.

The shift frequencies of the acousto-optic modulating devices 116-1 and 116-2 are +41 MHz and −40 MHz respectively, and as a result, the frequency of the reference beam 105 is shifted by 1 MHz.

Further, the dispersion compensating glass 115-2 performs dispersion compensation of lenses 120-1 and 120-2 which are used for scanning the eye 107.

Next, an optical path of the measuring beam 106 will be described.

The measuring beam 106, which is divided by the beam splitter 103-1 passes through a dispersion compensating glass 115-3, is reflected by a beam splitter 103-3 and is incident on the variable beam expander 136.

Here, the dispersion compensating glass 115-3 compensates dispersion of the acousto-optic modulating devices 116-1 and 116-2.

Further, the variable beam expander 136 has the function of changing a beam diameter of the measuring beam 106. For example, the beam diameter of 4 mm can be changed between 1 mm and 4 mm.

Next, the measuring beam 106 is incident on the mirror of the XY scanner 119.

Here, for simplification, the XY scanner 119 is illustrated as one mirror, but in reality, two mirrors that are an X scanning mirror and a Y scanning mirror are disposed to be close to each other to perform raster-scan over the retina 127 in the direction perpendicular to the optical axis. The center of the measuring beam 106 is regulated to correspond to the rotation center of the mirror of the XY scanner 119.

The lenses 120-1 and 120-2 are the optical system for scanning the retina 127, and have the function of scanning the measuring beam 106 over the retina 127 with the location near the cornea 126 as a pivot.

Here, the focal lengths of the lenses 120-1 and 120-2 are 50 mm and 50 mm, respectively.

When the measuring beam 106 is incident on the eye 107, the measuring beam 106 becomes the return beam 108 by being reflected and scattered by the retina 127.

Further, the return beam 108 is divided into the return beam (first return beam) 108-1 and the return beam (second return beam) 108-2 by the beam splitter 103-3, and the return beam 108-1 is transmitted by the beam splitter 103-1, and is guided to the detector 138.

Here, for example, an APD (Avalanche Photo Diode) which is a high-speed and high-sensitivity optical sensor is used as the detector 138.

The return beam 108-2 is guided to the balanced detector 122. An electric stage 117-2 can move in the direction illustrated by the arrow, and can regulate and control the position of the associated lens 120-2. Here, by adjusting the position of the lens 120-2 by using the electric stage 117-2, the lens 120-2 gathers the measuring beam 106 on the retina 127 even if the eye 107 of an examinee has refractive error so that the OCT device 100 can acquire the OCT image.

Next, a configuration of the measuring beam observation system which is the feature of the present invention will be described with use of FIGS. 1, 2A, and 2B.

In the OCT device 100, the retina 127 is irradiated with the measuring beam 106 through the cornea 126 as described above.

The observation camera 139 is installed for the purpose of observing the state of the measuring beam 106 being incident on the retina 127 through the cornea 126.

Here, the observation camera 139 is installed at a right side in front of the eye 107, but the observation camera 139 may be located at any position if only the observation camera 139 can observe the cornea 126 and its vicinity.

The observation camera 139 and the personal computer 125 are electrically connected so that the observation image acquired with the observation camera 139 is taken in the personal computer 125 and can be displayed and stored by linking the observation image and the OCT image with each other.

In correspondence with the wavelength of 830 nm of the measuring beam 106, a near-infrared camera is used as the observation camera 139. The near-infrared camera may be configured by combination of a near-infrared area sensor and a lens.

Next, an observation image 142 which is acquired by using the observation camera 139 will be described. FIGS. 2A and 2B illustrate views illustrating the observation images of the measuring beams of the OCT device which are acquired by using the observation camera in the present embodiment.

Figure 2A:
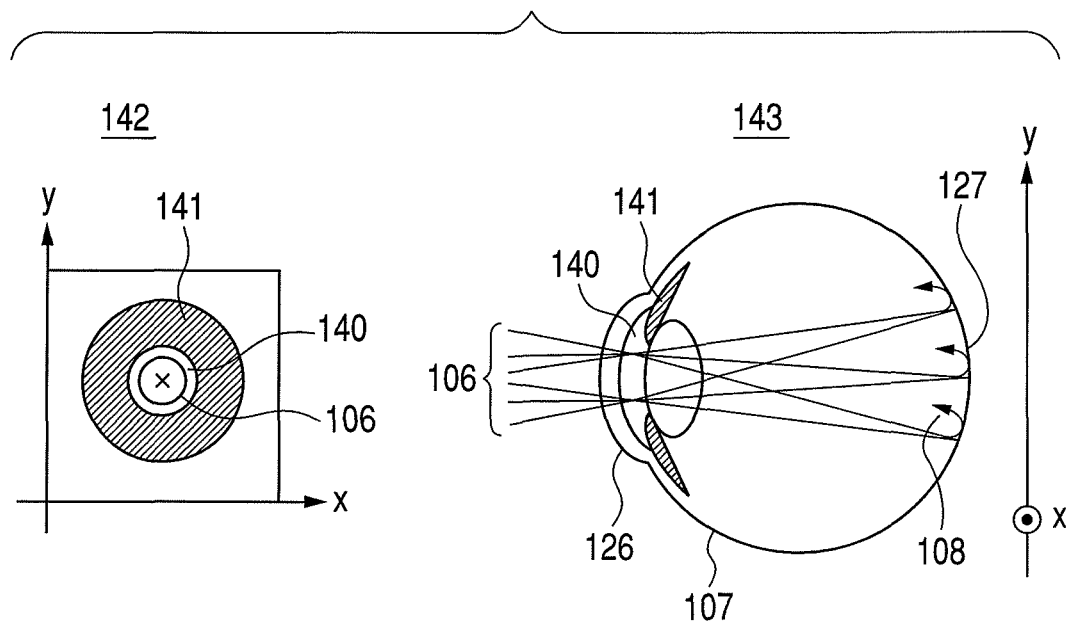
FIGS. 2A and 2B are views illustrating observation images of measuring beams of the OCT device which are acquired by an observation camera in embodiment 1 of the present invention.
Figure 2B:
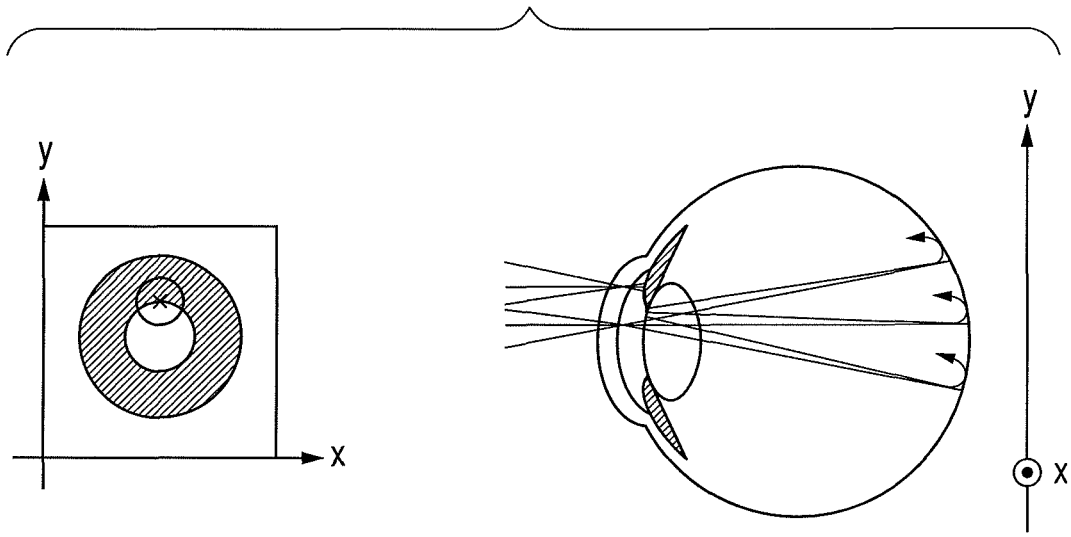

In each of FIGS. 2A and 2B, the same reference numerals and characters are assigned to the configurations which are the same as or corresponding to the configurations shown in FIG. 1, and therefore, the description of the redundant configurations will be omitted.

In each of FIGS. 2A and 2B, a pupil 140 and an iris 141 are illustrated.

In each of FIGS. 2A and 2B, the observation image 142 which is acquired by using the observation camera 139 is on the left side, whereas a schematic view 143 schematically expressing the section of the eye 107 which is the observation target is on the right side.

Further, the measuring beams 106 of FIGS. 2A and 2B have the same diameters and same energy. A plurality of measuring beams 106 drawn here shows the state of scanning the measuring beams 106 over the retina 127 by the XY scanner 119.

Here, the measuring beams 106 generally transmit through the pupil 140 easily, whereas the measuring beams 106 hardly transmit through the iris 141.

In FIG. 2A, the measuring beam 106 transmits through the pupil 140 without the iris 141 being irradiated with the measuring beam 106, and the retina 127 is irradiated with the measuring beam 106.

This state is suitable for imaging because the measuring beam 106 forms an image on the retina 127.

In contrast with this, FIG. 2B illustrates the state in which the iris 141 is irradiated with a part of the measuring beam 106, and the retina 127 is not properly irradiated with the measuring beam 106.

In the state of FIG. 2B, the energy of the measuring beam 106 with which the retina 127 is irradiated becomes small as compared with the state of FIG. 2A.

Generally, there is an upper limit to the energy of the measuring beam with which the retina is irradiated.

Therefore, in the state of FIG. 2B, the return beam 108 becomes small, as a result of which, the S/N ratio of an interfering signal which will be described later for configuring a tomographic image becomes low, as compared with the state of FIG. 2A.

Therefore, in order to acquire a tomographic image suitable for diagnosis, it is important to cause the measuring beam 106 to be properly incident on the pupil 140.

Further, even if the iris 141 is inevitably irradiated with the measuring beam 106 for the reason of difficulty in keeping the examinee standing still, the observation image 142 which is obtained by using the observation camera 139 can be used as the following unit.

Specifically, the observation image 142 can be used as the unit for evaluating reliability of the acquired tomographic image, or as the unit for determining whether or not imaging of the tomographic image is stopped or remeasurement is performed.

Next, a configuration of a measuring system in the OCT device in the present embodiment will be described.

The OCT device 100 can acquire the tomographic image (OCT image) which is configured by the intensity of the interfering signal by the Mach-Zehnder interferometer.

Describing the measuring system, the return beam 108 which is the beam reflected and scattered at the retina 127 is divided into the return beam 108-1 and the return beam 108-2 by the beam splitter 103-3.

Of the divided return beams, the return beam 108-2 is further divided by the beam splitter 103-2. Meanwhile, the reference beam 105 is also divided by the beam splitter 103-2.

Here, the reference beam 105 and the return beam 108-2 are regulated to be combined behind the beam splitter 103-2.

The combined beams are gathered by the lenses 111-2 and 111-3, and are guided to the balanced detector 122 through the optical fibers 110-2 and 110-3 so that the intensity of the beam which is the result of combining the reference beam 105 and return beam 108-2 is converted into a voltage.

The obtained voltage signal is amplified by the amplifier 123, a necessary frequency component is taken out by the filter 124, demodulation and data processing are performed in the personal computer 125, and the tomographic image is formed.

Here, the reference beam 105 is shifted by a frequency of 1 MHz, as described above.

Therefore, the above described obtained voltage signal becomes a beat signal of 1 MHz. Thus, though the return beam 108-2 is usually extremely weak, the detection sensitivity can be increased because the reference beam 105 is large.

As the above described filter 124, a bandpass filter of 1 MHz is used so that the beat signal is detected with high sensitivity by cutting unwanted frequency components.

The return beam 108-1 of the return beams divided by the beam splitter 103-3 described above passes through the beam splitter 103-1, is gathered by the lens 111-4, passes through the optical fiber 110-4 and is guided to the detector 138.

The detector 138 is electrically connected to the personal computer 125 as the above described interfering signal so that the intensity of the return beam 108-1 can be recorded and displayed.

The signal obtained by the detector 138 is an intensity signal of the return beam 108-1 reflected and scattered by the retina 127, and does not have depth resolution unlike the above described interfering signal.

Next, an acquiring method of a tomographic image and an observation image using the OCT device of the present embodiment which is the feature of the present invention will be described by using FIGS. 1, 3A, 3B, 3C, 4A, 4B, 4C and 4D.

Figure 3A:
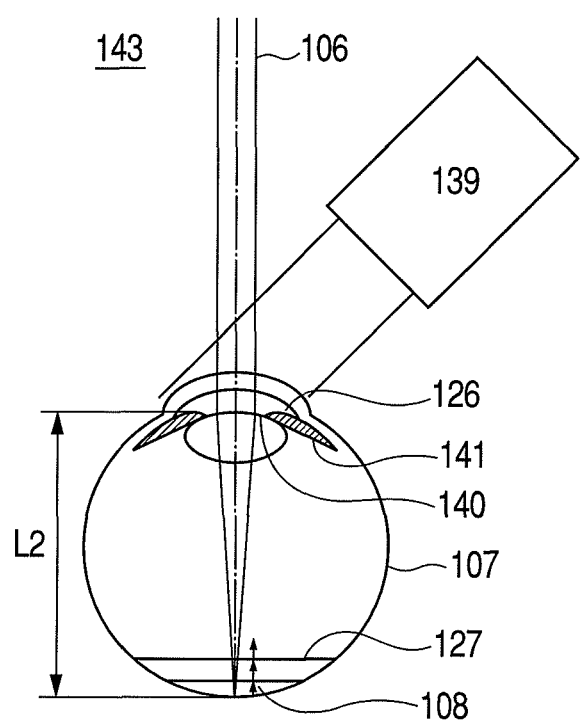
FIGS. 3A, 3B, and 3C are schematic views illustrating an acquiring method of a tomographic image of the OCT device in embodiment 1 of the present invention.
Figure 3B:
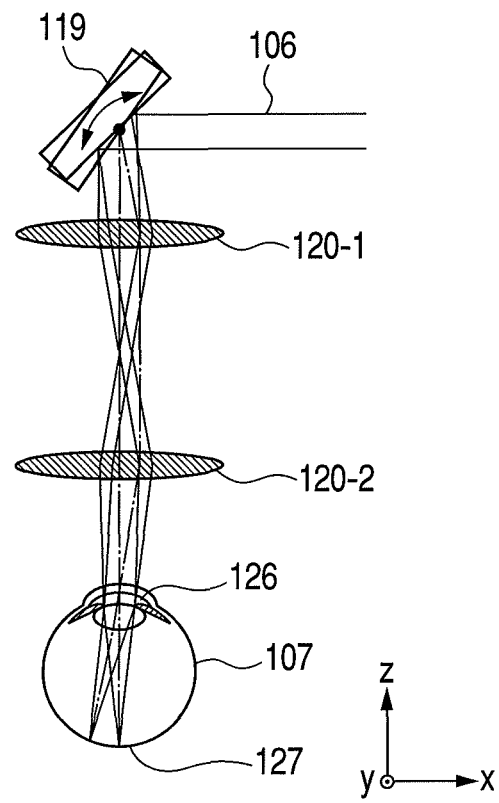
Figure 3C:
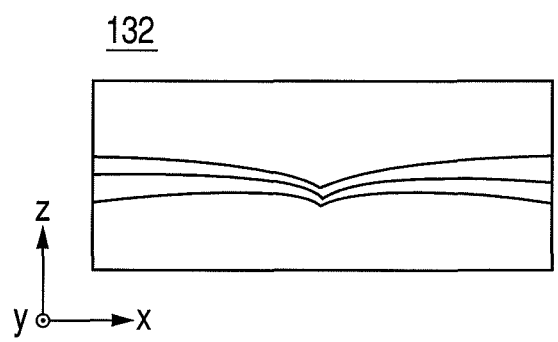

FIGS. 3A, 3B, and 3C illustrate schematic views illustrating the acquiring method of the tomographic image of the OCT device in the present embodiment.

Further, FIGS. 4A, 4B, 4C, and 4D illustrate views illustrating an evaluation method of the observation image of the OCT device in the present embodiment.

In FIGS. 3A, 3B, 3C, 4A, 4B, 4C, and 4D, the same reference numerals and characters are assigned to the same or corresponding configurations as or to the configurations illustrated in FIGS. 1, 2A, and 2B, and therefore, the description of the redundant configurations will be omitted.

The OCT device 100 can acquire the tomographic image of a desired site of the retina 127 by controlling the electric stage 117-1 and the XY scanner 119 (FIG. 1).

Here, an example of acquiring the tomographic image (surface parallel with the optical axis) of the retina 127 will be described. FIG. 3A is a schematic view 143 of the eye 107, and illustrates the state observed by the OCT device 100. Further, FIG. 3A also illustrates the state of the measuring beam 106 being incident on the pupil 140 by the observation camera 139.

First, a method for configuring a tomographic image will be described.

As shown in FIG. 3A, the measuring beam 106 becomes the return beam 108 by being reflected and scattered at various positions when incident on the retina 127 through the cornea 126, and the measuring beam 106 reaches the balanced detector 122 (FIG. 1) with time delays in the respective positions. Here, since the bandwidth of the light source 101 is wide, and the coherence length is short, an interfering signal can be detected in the balanced detector 122 only when the optical path length of the reference beam path and the optical path length of the measuring beam path are equal.

The frequency of the reference beam 105 is shifted by 1 MHz with respect to the measuring beam 106 as described above, and therefore, the interfering signal becomes a beat signal of 1 MHz.

Further, as shown in FIG. 3B, when the interfering signal is detected while the X-axis of the XY scanner 119 is driven, the interfering signal becomes a signal having the positional information of the X-axis.

By squaring the amplitude of this signal and demodulating the signal, the intensity distribution in the X-axis direction in an arbitrary XY-plane of the return beam 108 is obtained.

Further, if the similar operation is repeated while the optical path length of the reference beam path is moved by using the electric stage 117-1, the two-dimensional distribution of the intensity of the return beam 108 in the XZ-plane is obtained, and a tomographic image 132 as shown in FIG. 3C is obtained.

The tomographic image 132 is originally such that the intensities of the return beams 108 from the retina 127 are arranged in an array form, and is displayed by fitting the intensities of the return beams 108 to the gray scale, for example, as described above, but only the borders are displayed in this case.

Next, a method for configuring the observation image will be described.

At the same time when the tomographic image described above is acquired, the observation camera 139 acquires the observation image showing the state of the measuring beam 106 being incident on the cornea 126.

It requires a time of about 0.01 to 1 seconds to acquire one tomographic image described above, and during this time, the observation camera 139 acquires one or a plurality of observation images, and displays or stores the observation images by linking the observation images with the above described tomographic images.

Next, an evaluating method of the observation image which is the feature of the present invention will be concretely described by using FIGS. 4A, 4B, 4C, and 4D.

Figure 4A:
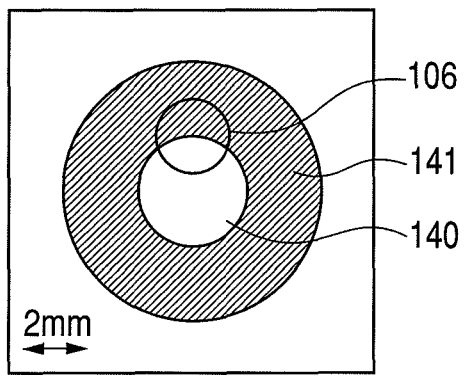
FIGS. 4A, 4B, 4C, and 4D are views illustrating an evaluating method of observation image of the OCT device in embodiment 1 of the present invention.

FIG. 4A illustrates the state of observing the retina (not illustrated) by transmitting the measuring beam 106 through the pupil 140.

When the retina of an eyeground is observed, observation is performed by scanning the measuring beam over the retina with the cornea as the pivot (FIG. 3B).

Therefore, the measuring beam 106 is observed as if the measuring beam 106 did not move on the cornea 126 while the tomographic image is being acquired. However, this does not apply to the case where the examinee is not standing still sufficiently.

In the present evaluating method, the following steps are successively performed, for example.

Alternatively, the steps can be properly performed by returning to the previous steps, and the following steps may be configured to be automatically performed by using control software.

The following steps are described on the precondition of performing image processing using a personal computer, but an operator may manually perform the similar operation by visually observing the observation image 142.

Figure 4B:
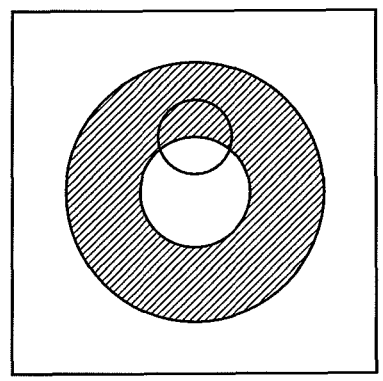

First, in a first step, the observation image 142 is acquired by using the observation camera 139 (FIG. 4B).

Next, in a second step, the acquired observation image 142 is taken in the personal computer 125 and is displayed and stored.

Figure 4C:
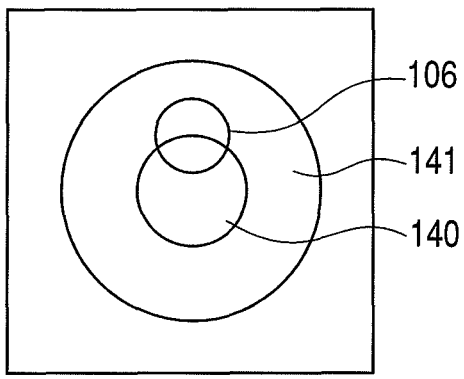

Next, in a third step, the observation image 142 is segmented by using the personal computer 125, and image recognition of the pupil 140, iris 141 and measuring beam 106 is performed (FIG. 4C).

Figure 4D:
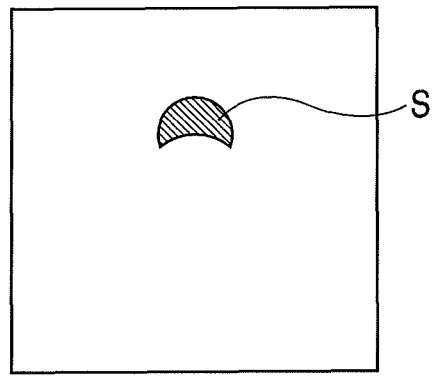

Next, in a fourth step, the logical product of the measuring beam 106 and the iris 141 of which images are recognized is taken, and its area S is calculated (FIG. 4D).

Next, in a fifth step, the tomographic image is evaluated in accordance with the value of the area S, and is ranked, and the tomographic image, the observation image 142 and the rank are displayed or stored by being linked with one another. Ranking is set as follows, for example.

A: $S=0$ mm$^2$, B: $0<S\leq1$ mm$^2$, C: $1<S\leq2$ mm$^2$, D: $S>2$ mm$^2$.

Next, in a sixth step, when the rank obtained in the above described fifth step is C or D, imaging of the tomographic image is stopped or the tomographic image is re-imaged (re-measured). In the above described fourth to fifth steps, the area S described above is used as the index of evaluation, but other indexes may be used.

For example, the center distance of the measuring beam 106 and the iris 141, and the shape of the logical product of the measuring beam 106 and the iris 141 can be used.

Similarly, the area and shape of the logical product of the measuring beam 106 and the pupil 140, and the center distance of the measuring beam 106 and the pupil 140 can be used. In such a case, ranking is properly set.

Embodiment 2

In embodiment 2, a configuration example of configuring any of the optical paths shown in embodiment 1 by an optical fiber will be described.

Figure 5:
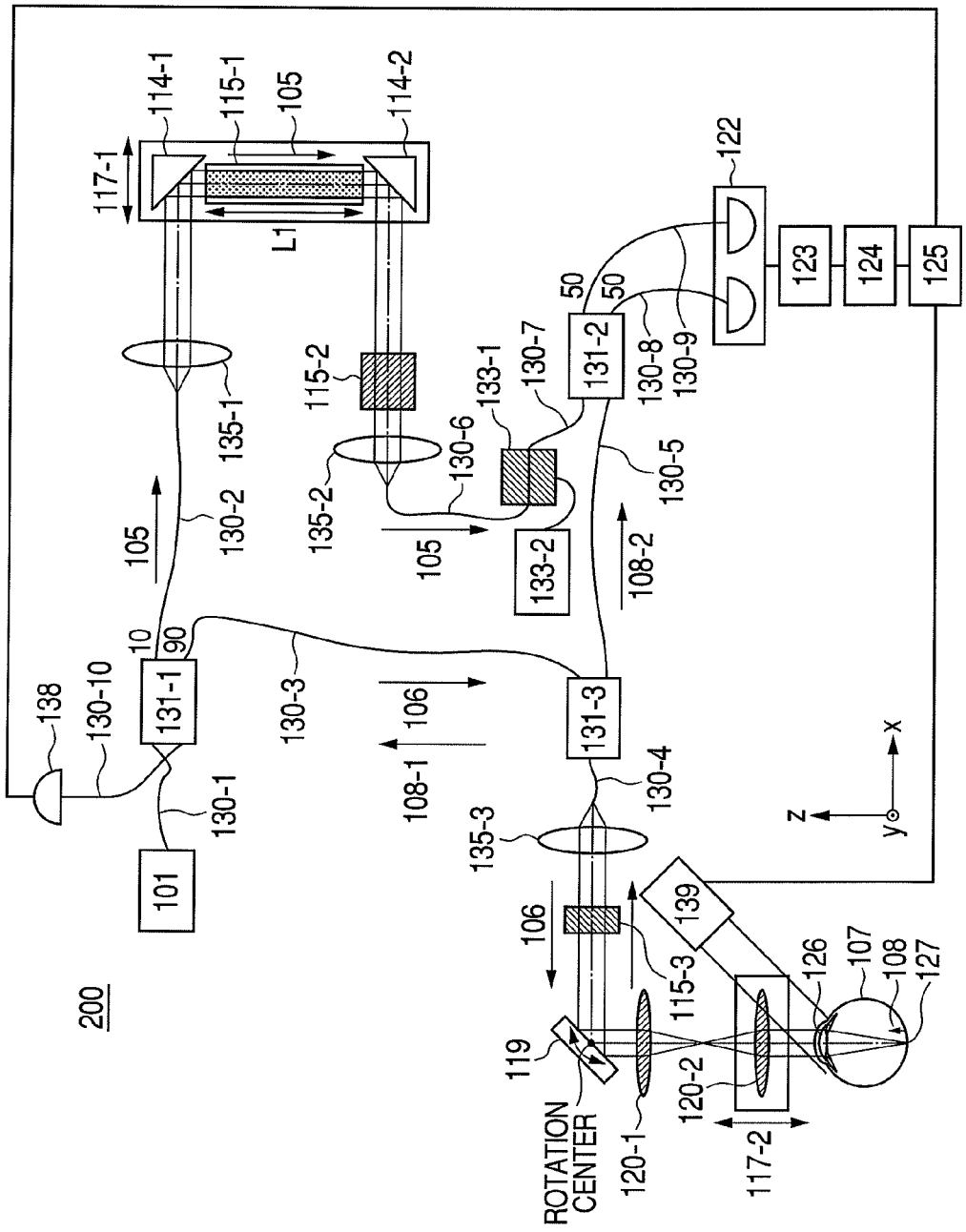
FIG. 5 is a view illustrating a schematic configuration of an entire optical system of the OCT device in embodiment 2 of the present invention.

FIG. 5 illustrates a view describing a schematic configuration of an entire optical system of an OCT device in the present embodiment.

In FIG. 5, the same reference numerals and characters are assigned to the same or corresponding configurations as or to the configurations of embodiment 1 shown in FIG. 1, and therefore, description of the redundant configurations will be omitted.

In FIG. 5, an OCT device 200, single-mode fibers 130 and optical couplers 131 are set.

In the present embodiment, the OCT device 200 is used as the device for acquiring a tomographic image of the retina 127 of the eye 107 in an examined eye.

In the present embodiment, the device is made compact by configuring a part of the optical system by using an optical fiber.

Except for use of the optical fiber, the present embodiment includes a configuration which does not differ from embodiment 1 in the basic configuration.

The OCT device 200 of the present embodiment configures a Mach-Zehnder interferometer as a whole as shown in FIG. 5.

In FIG. 5, the measuring beam 106 becomes the return beam 108 by being reflected and scattered by the eye 107 which is an observation target to be returned, and thereafter, is combined with the reference beam 105 by an optical coupler 131-2.

The reference beam 105 and the return beam 108 are combined with each other, and thereafter, are divided and are incident on the balanced detector 122. The tomographic image of the eye 107 is configured by using the light intensity obtained by the balanced detector 122.

Next, the light source 101 and its periphery will be described.

The light source 101 itself is similar to that of embodiment 1. The light emitted from the light source 101 is guided to an optical coupler 131-1 through a single-mode fiber 130-1, and is divided at an intensity ratio of 90:10 to be the measuring beam 106 and the reference beam 105.

Next, an optical path of the reference beam 105 will be described.

After divided by the optical coupler 131-1, the reference beam 105 is guided to a lens 135-1 through a single-mode fiber 130-2, and is regulated to be parallel beams with a beam diameter of 4 mm.

The electric stage 117-1 and the mirrors 114-1 and 114-2 associated with the electric stage 117-1, and the dispersion compensating glass 115-1 are the same as those in embodiment 1, and description of them will be omitted.

After passing through the dispersion compensating glass 115-2, the reference beam 105 is guided to a single-mode fiber 130-6 by using a lens 135-2.

Further, the reference beam 105 passes through the acousto-optic modulating device 133-1 and a single-mode fiber 130-7, and is incident on the optical coupler 131-2.

Here, the acousto-optic modulating device 133-1 is for an optical fiber, and frequency shift of 1 MHz can be performed by using the controller 133-2. Accordingly, the reference beam 105 obtained here is similar to that of embodiment 1.

Next, an optical path of the measuring beam 106 will be described.

The measuring beam 106 which is divided by the optical coupler 131-1 passes through a single-mode fiber 130-3 and is incident on an optical coupler 131-3.

Thereafter, the measuring beam 106 passes through a single-mode fiber 130-4, is guided to a lens 135-3, and is regulated to be parallel beams with a beam diameter of 4 mm.

Further, the measuring beam 106 passes through the dispersion compensating glass 115-3, and thereafter, is incident on the mirror of the XY scanner 119. The optical system between the XY scanner 119 and the eye 107 is similar to that of embodiment 1, and therefore, description thereof will be omitted.

Here, the dispersion compensating glass 115-3 compensates dispersion of the acousto-optic modulating device 133-1.

Here, the measuring beam 106 goes to and returns from the dispersion compensating glass 115-3, and therefore, the thickness of the dispersion compensating glass 115-3 is half the thickness of the glass portion of the acousto-optic modulating device 133-1. When the measuring beam 106 is incident on the eye 107, the measuring beam 106 becomes the return beam 108 by being reflected and scanned by the retina 127.

Further, the return beam 108 passes through the optical coupler 131-3, and is guided to the optical coupler 131-2.

Next, a configuration of a measuring beam observing system which is the feature of the present invention will be described.

In the OCT device 200, the measuring beam 106 passes through the cornea 126 and the retina 127 is irradiated with the measuring beam 106 as described above.

The observation camera 139 is installed for the purpose of observing the state of the measuring beam 106 being incident on the retina 127 through the cornea 126. The details of the configuration and the observation image of the measuring beam observation system are similar to those of embodiment 1, and description of them will be omitted.

Next, a configuration of the measuring system in the OCT device of the present embodiment will be described.

The OCT device 200 can acquire a tomographic image (OCT image) configured by the intensity of the interfering signal by the Mach-Zehnder interferometer.

The measuring system will be described. The return beam 108-2 which is one of the return beams 108 that are the beams reflected and scattered by the retina 127 is combined with the reference beam 105 by the optical coupler 131-2, and is further divided at 50:50.

Next, the beam passes through single-mode fibers 130-8 and 130-9, and is guided to the balanced detector 122.

The intensity of the beams in which the reference beam 105 and the return beam 108 are combined is converted into a voltage.

The obtained voltage signal is amplified by the amplifier 123, and the required frequency component is taken out by the filter 124, demodulation and data processing are performed in the personal computer 125, and the tomographic image is formed.

Further, the other return beam 108-1 of the return beams 108 described above passes through the optical coupler 131-1, and passes through the optical fiber 130-10 to be guided to the detector 138.

Further, the detector 138 is electrically connected to the personal computer 125 as the above described interfering signal so that the intensity of the return beam 108-1 can be recorded and displayed.

The signal obtained by the detector 138 is the intensity signal of the return beam 108-1 by being reflected and scattered by the retina 127, and does not have depth resolution unlike the above described interfering signal.

An acquiring method of a tomographic image using the OCT device of the present embodiment will be described. The OCT device 200 can acquire a tomographic image of a desired site of the retina 127 by controlling the two electric stages 117-1 and 117-2 and the XY scanner 119.

The details of the obtaining method and the evaluating method of a tomographic image and an observation image are the same as those in embodiment 1, and therefore, description of them will be omitted.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-130392, filed May 19, 2008 which is hereby incorporated by reference herein in its entirety.

What is claimed is:

1. An optical coherence tomographic imaging apparatus comprising:
    a tomographic image acquiring unit configured to acquire a tomographic image of a fundus of an eye by using a return beam of a measuring beam, which is reflected or scattered by the eye, and a reference beam corresponding to the measuring beam;
    a non-tomographic observation image acquiring unit configured to acquire a non-tomographic observation image of an anterior ocular segment of the eye, wherein the non-tomographic observation image corresponds to the tomographic image;
    an information acquiring unit configured to acquire information of a region of overlap between an irradiation region of the measuring beam in the anterior ocular segment and an iris region of the anterior ocular segment based on the non-tomographic observation image; and an evaluating unit configured to evaluate the tomographic image based on the information of the region.

2. The optical coherence tomographic imaging apparatus according to claim 1, further comprising a determination unit configured to determine to stop imaging of a new tomographic image or to re-image a new tomographic image based on an evaluation by said evaluating unit.

3. The optical coherence tomographic imaging apparatus according to claim 1, wherein said information acquiring unit acquires any one of an area of the measuring beam with which a portion except for a pupil of the eye is irradiated, a relative distance between the pupil of the eye and the measuring beam, and a shape of the measuring beam in a portion irradiated with the measuring beam except for the pupil of the eye as the information.

4. The optical coherence tomographic imaging apparatus according to claim 3, wherein said evaluating unit ranks the tomographic image, which is linked with the non-tomographic observation image, based one of the area of the measuring beam with which the portion except for the pupil of the eye is irradiated, the relative distance between the pupil of the eye and the measuring beam, and the shape of the measuring beam in the portion irradiated with the measuring beam except for the pupil of the eye.

5. The optical coherence tomographic imaging apparatus according to claim 1, wherein said non-tomographic observation image acquiring unit is any one of an infrared camera, an area sensor, and a confocal microscope.

6. The apparatus according to claim 1, further comprising:
a segmentation unit configured to segment the irradiation region and the iris region from the non-tomographic observation image,
wherein the information acquiring unit acquires the information based on the segmented irradiation region and the segmented iris region.

7. The apparatus according to claim 1, further comprising a display controlling unit configured to control a display unit to display the tomographic image and the non-tomographic observation image corresponding to the tomographic image side-by-side.

8. The apparatus according to claim 1,
wherein said information acquiring unit acquires the value regarding the overlap region as the information, and
wherein said evaluating unit evaluates the tomographic image in accordance with the value.

9. An optical coherence tomographic imaging apparatus, comprising:
a non-tomographic observation image acquiring unit configured to acquire a non-tomographic observation image of an anterior ocular segment of an eye;
a detection unit configured to detect a combined beam of a return beam, which is the measuring beam reflected or scattered by a fundus of the eye, and a reference beam; and
a tomographic image acquiring unit configured to acquire a tomographic image of the fundus from the combined beam detected by said detection unit, wherein the non-tomographic observation image is configured in a manner that links with the tomographic image obtained by irradiating the anterior ocular segment with the measuring beam, wherein the non-tomographic observation image corresponds to the tomographic image;
an information acquiring unit configured to acquire information of a region of overlap between an irradiation region of the measuring beam in the anterior ocular segment and an iris region of the anterior ocular segment based on the non-tomographic observation image; and
a determination unit configured to determine to stop imaging of a new tomographic image of the fundus or to re-image a new tomographic image of the fundus based on the information of the region.

10. The optical coherence tomographic imaging apparatus according to claim 9, further comprising a display controlling unit configured to control a display unit to display the non-tomographic observation image and the tomographic image which are linked with each other.

11. The optical coherence tomographic imaging apparatus according to claim 9, further comprising:
a light source;
a dividing unit configured to divide a light from the light source into the measuring beam which is incident on the eye, and the reference beam which is incident on a reference unit; and
a combining unit configured to combine the return beam from the eye and the reference beam reflected by said reference unit,
wherein intensity information relating to a cross-sectional position of the eye in an optical axis direction of an optical system is configured to be acquired.

12. An optical coherence tomographic imaging method comprising the steps of:
acquiring a non-tomographic observation image of an anterior ocular segment of an eye;
acquiring a tomographic image of a fundus of the eye based on a return beam from the eye irradiated by a measuring beam, wherein the non-tomographic observation image corresponds to the tomographic image;
acquiring information of a region of overlap between an irradiation region of the measuring beam in the anterior ocular segment and an iris region of the anterior ocular segment based on the non-tomographic observation image; and
evaluating the tomographic image based on the information of the region.

13. A non-transitory computer-readable storage medium storing a program for causing a computer to execute the method according to claim 12.

14. The method according to claim 12, further comprising the step of determining to stop imaging of the tomographic image or to re-image the tomographic image based on an evaluation performed in said evaluating step.

15. The method according to claim 12, further comprising the step of:
segmenting the irradiation region and the iris region from the non-tomographic observation image,
wherein said information acquiring step acquires the information based on the segmented irradiation region and the segmented iris.

16. The method according to claim 12,
wherein the value regarding the overlap region as the information is acquired in said information acquiring step, and
wherein the tomographic image is evaluated in said evaluating step in accordance with the value.

17. An optical coherence tomographic imaging method comprising the steps of:
acquiring a non-tomographic observation image of an anterior ocular segment of an eye;
detecting a combined beam of a return beam, which is the measuring beam reflected or scattered by a fundus of the eye, and a reference beam;
acquiring a tomographic image of the fundus of the eye from the combined beam detected by said detecting step, wherein the non-tomographic observation image is configured in a manner that links with the tomographic image obtained by irradiating the anterior ocular segment with the measuring beam, wherein the non-tomographic observation image corresponds to the tomographic image;

acquiring information of a region of overlap between an irradiation region of the measuring beam in the anterior ocular segment and an iris region of the anterior ocular segment based on the non-tomographic observation image; and determining to stop imaging of a new tomographic image of the fundus or to re-image a new tomographic image of the fundus based on the information of the region.

\* \* \* \* \*